US012270775B2

(12) United States Patent
Sakurai et al.

(10) Patent No.: US 12,270,775 B2
(45) Date of Patent: Apr. 8, 2025

(54) SENSOR

(71) Applicant: NABTESCO CORPORATION, Tokyo (JP)

(72) Inventors: Kazuhiko Sakurai, Tsu (JP); Masaki Harada, Tsu (JP)

(73) Assignee: NABTESCO CORPORATION, Tokyo (JP)

( * ) Notice: Subject to any disclaimer, the term of this patent is extended or adjusted under 35 U.S.C. 154(b) by 137 days.

(21) Appl. No.: 17/598,708

(22) PCT Filed: Apr. 26, 2019

(86) PCT No.: PCT/JP2019/018107
§ 371 (c)(1),
(2) Date: Sep. 27, 2021

(87) PCT Pub. No.: WO2020/217508
PCT Pub. Date: Oct. 29, 2020

(65) Prior Publication Data
US 2022/0178857 A1  Jun. 9, 2022

(51) Int. Cl.
*G01N 27/04* (2006.01)
*G01N 33/28* (2006.01)

(52) U.S. Cl.
CPC ......... *G01N 27/04* (2013.01); *G01N 33/2835* (2013.01)

(58) Field of Classification Search
CPC ............. G01N 27/07; G01N 33/2858; G01N 33/2888; G01N 33/2835
USPC ....................................................... 324/693
See application file for complete search history.

(56) References Cited

U.S. PATENT DOCUMENTS

| | | | | |
|---|---|---|---|---|
| 5,179,346 A | * | 1/1993 | McGee | G01N 15/0656 |
| | | | | 324/693 |
| 5,402,113 A | * | 3/1995 | Naas | G01N 33/2858 |
| | | | | 324/698 |
| 7,112,973 B2 | * | 9/2006 | Itomi | G01N 33/2888 |
| | | | | 73/61.42 |
| 7,151,383 B2 | * | 12/2006 | Itomi | G01N 33/2888 |
| | | | | 73/61.42 |
| 10,317,354 B2 | * | 6/2019 | Ricci | G01N 27/041 |
| 10,359,077 B2 | * | 7/2019 | Ito | F16C 19/383 |

(Continued)

FOREIGN PATENT DOCUMENTS

| | | | | | |
|---|---|---|---|---|---|
| CN | 111855755 A | * | 10/2020 | ......... | G01N 15/0606 |
| CN | 112782237 A | * | 5/2021 | .......... | B25J 19/0062 |

(Continued)

OTHER PUBLICATIONS

JP 2011-203093 A english translation (Year: 2011).*

(Continued)

*Primary Examiner* — Reena Aurora
(74) *Attorney, Agent, or Firm* — Pillsbury Winthrop Shaw Pittman, LLP

(57) ABSTRACT

A sensor includes a plurality of detecting units and a sensing unit. Each of the detecting units includes a pair of electrodes and a detecting area formed between the electrodes, and is configured to cause a change in electrical resistance between the electrodes as conductive particles accumulate. The sensing unit outputs a sensing signal if at least two or more of the detecting units experience a change in electrical resistance.

7 Claims, 8 Drawing Sheets

(56) References Cited

U.S. PATENT DOCUMENTS

| | | | | |
|---|---|---|---|---|
| 10,705,038 B2 * | 7/2020 | Ricci | | G01N 27/06 |
| 10,705,039 B2 * | 7/2020 | Kiriyama | | G01N 33/2858 |
| 11,249,041 B2 * | 2/2022 | Amamiya | | G01N 27/226 |
| 11,346,871 B2 * | 5/2022 | Harada | | B25J 19/02 |
| 11,499,931 B2 * | 11/2022 | Sakurai | | G01N 33/2858 |
| 2002/0145530 A1 * | 10/2002 | Sato | | G01N 33/2858 340/540 |
| 2005/0212533 A1 * | 9/2005 | Itomi | | G01N 33/2888 324/698 |
| 2006/0125487 A1 * | 6/2006 | Itomi | | G01N 33/2888 324/533 |
| 2009/0314064 A1 * | 12/2009 | Augros | | F01M 11/10 73/61.42 |
| 2012/0103057 A1 | 5/2012 | Kimata et al. | | |
| 2018/0031504 A1 * | 2/2018 | Ricci | | G01N 33/22 |
| 2018/0223907 A1 * | 8/2018 | Ito | | F16C 33/667 |
| 2018/0275083 A1 * | 9/2018 | Kiriyama | | G01N 33/2858 |
| 2019/0128789 A1 | 5/2019 | Asmus et al. | | |
| 2019/0154608 A1 * | 5/2019 | Nakamura | | G01N 33/2888 |
| 2019/0257777 A1 * | 8/2019 | Ricci | | G01N 27/041 |
| 2020/0057044 A1 * | 2/2020 | Nakamura | | G01N 33/2888 |
| 2020/0080953 A1 | 3/2020 | Yamakoshi et al. | | |
| 2020/0340936 A1 * | 10/2020 | Sakurai | | G01N 27/07 |
| 2021/0132126 A1 * | 5/2021 | Harada | | G01R 27/16 |
| 2021/0148847 A1 * | 5/2021 | Amamiya | | A47J 37/1266 |
| 2021/0181177 A1 * | 6/2021 | Sakurai | | G01N 15/0606 |
| 2021/0263009 A1 * | 8/2021 | Shenouda | | G01V 3/101 |
| 2022/0178857 A1 * | 6/2022 | Sakurai | | G01N 15/0656 |
| 2022/0291159 A1 * | 9/2022 | Harada | | G01N 33/2858 |
| 2022/0291188 A1 * | 9/2022 | Kurita | | G01N 27/07 |
| 2023/0035518 A1 * | 2/2023 | Sakurai | | G01N 33/2888 |

FOREIGN PATENT DOCUMENTS

| | | | | |
|---|---|---|---|---|
| CN | 112986337 A * | 6/2021 | | G01N 15/0606 |
| CN | 113574130 A * | 10/2021 | | |
| DE | 102013212696 A1 * | 12/2014 | | G01N 33/2858 |
| DE | 102018204674 A1 * | 9/2018 | | G01N 15/0606 |
| DE | 102018219895 A1 * | 5/2019 | | F16H 55/02 |
| DE | 102018219625 A1 * | 5/2020 | | G01N 15/0606 |
| DE | 102020205944 A1 * | 11/2021 | | G01N 15/0656 |
| DE | 102021117863 A1 * | 1/2023 | | |
| EP | 3742162 A2 * | 11/2020 | | G01N 15/0606 |
| EP | 3783348 A1 * | 2/2021 | | A47J 37/1266 |
| EP | 3819635 A1 * | 5/2021 | | B25J 19/0062 |
| EP | 3839504 A2 * | 6/2021 | | G01N 15/0606 |
| EP | 3961201 A1 * | 3/2022 | | G01N 27/04 |
| EP | 4056986 A1 * | 9/2022 | | G01N 27/07 |
| EP | 4056987 A1 * | 9/2022 | | G01N 27/07 |
| FR | 2927401 A1 * | 8/2009 | | B03C 1/282 |
| JP | 01-235107 A | 9/1989 | | |
| JP | 6-148109 A | 5/1994 | | |
| JP | 2002286697 A * | 10/2002 | | |
| JP | 2002310967 A * | 10/2002 | | G01N 33/2858 |
| JP | 2005331324 A | 12/2005 | | |
| JP | 2005337938 A * | 12/2005 | | |
| JP | 2005337945 A * | 12/2005 | | |
| JP | 2005337981 A * | 12/2005 | | |
| JP | 2006052989 A * | 2/2006 | | |
| JP | 2006170667 A * | 6/2006 | | G01N 33/2888 |
| JP | 2006300606 A * | 11/2006 | | |
| JP | 2006300608 A * | 11/2006 | | |
| JP | 2010-014518 A | 1/2010 | | |
| JP | 2011007610 A * | 1/2011 | | G01N 33/2888 |
| JP | 4643243 B2 * | 3/2011 | | G01N 33/2888 |
| JP | 4711723 B2 * | 6/2011 | | |
| JP | 2011203093 A * | 10/2011 | | G01N 15/0656 |
| JP | 2012-013639 A | 1/2012 | | |
| JP | 2012-093287 A | 5/2012 | | |
| JP | 2017-190813 A | 10/2017 | | |
| JP | 2018-163133 A | 10/2018 | | |
| JP | 2018-200299 A | 12/2018 | | |
| JP | 2019-507880 A | 3/2019 | | |
| JP | 2019128311 A * | 8/2019 | | |
| JP | 2020183932 A * | 11/2020 | | G01N 15/0606 |
| JP | 2021057188 A * | 4/2021 | | |
| JP | 2021076386 A * | 5/2021 | | B25J 19/0062 |
| JP | 2021096168 A * | 6/2021 | | G01N 15/0606 |
| KR | 10-2016-0116738 A | 10/2016 | | |
| KR | 20210054446 A * | 5/2021 | | |
| KR | 20210077590 A * | 6/2021 | | |
| KR | 20220005467 A * | 1/2022 | | |
| WO | WO-2010150688 A1 * | 12/2010 | | G01N 33/2888 |
| WO | WO-2020004273 A1 * | 1/2020 | | B32B 7/025 |
| WO | WO-2020217508 A1 * | 10/2020 | | G01N 27/04 |

OTHER PUBLICATIONS

Extended European Search Report dated Oct. 10, 2022, issued in corresponding European Patent Application No. 19926223.9 (54 pgs.).

International Search Report dated Jul. 23, 2019, issued in corresponding International Application No. PCT/JP2019/018107 with English translation (5 pgs.).

Notice of Reasons for Refusal dated Sep. 28, 2021, issued in corresponding Japanese Patent Application No. 2018-011484 with English translation (9 pgs.).

Office Action dated Nov. 14, 2023, issued in corresponding Chinese Patent Application No. 201980095788.X with English translation (13 pgs.).

Office Action dated Sep. 22, 2022, issued in corresponding Taiwanese Patent Application No. 108114920 with English translation (13 pgs.).

Second Office Action dated Mar. 20, 2024, issued in corresponding Chinese Patent Application No. 201980095788.X with English translation (10 pgs.).

* cited by examiner

SENSOR

CROSS-REFERENCE TO RELATED APPLICATIONS

This application is the U.S. National Phase Application of PCT/JP2019/18107, filed on Apr. 26, 2019, the contents of which is incorporated herein by reference in it's entirety.

TECHNICAL FIELD

The present invention relates to a sensor.

BACKGROUND

A mechanical device such as a speed reducer is housed in a housing filled with a lubricant oil in order to prevent the mechanical parts such as gears from being damaged. If the mechanical parts are worn out during operation of the mechanical device, abrasion powder is mixed into the lubricant oil. The abrasion powder is, for example, a conductive substance such as iron powder. As the mechanical parts are increasingly worn out and enter a wear-out failure period, which is defined in a failure rate curve (a bathtub curve), an increased amount of abrasion powder is mixed into the lubricant oil. For this reason, a sensor for sensing the amount of the abrasion powder in the lubricant oil allows for accurate preventive maintenance of the mechanical parts.

For example, Patent Literature 1 discloses an oil check sensor, which can be used for the above purposes. The disclosed oil check sensor is mounted to, for example, a transmission of an automobile and configured to check, for example, deterioration of an oil in an oil container and the degree of wear of mechanical parts lubricated with the oil. This sensor includes a pair of electrodes and a magnet for attracting iron powder or the like contained in the oil. Based on the resistance between the electrodes, which depends on the conductive substance attracted, the sensor senses the amount of the conductive substance in the oil.

RELEVANT REFERENCES

List of Relevant Patent Literature

Patent Literature 1: Japanese Patent Application Publication No. 2002-286697

SUMMARY

During manufacturing of the mechanical device, foreign matter having a large particle diameter (for example, a cutting chip or the like) may be generated by cutting or the like, and may adhere to constituent components of the mechanical device and be mixed into a lubricant oil. If such foreign matter having a large particle size adheres to the sensor, a short circuit occurs between the paired electrodes even with little abrasion powder produced. For the reasons stated above, the sensor for sensing the amount of abrasion powder may operate unexpectedly even when a small amount of abrasion powder is produced.

One object of the present invention is to provide a sensor capable of inhibiting an unexpected operation caused by admixture of foreign matter. Other objects of the present invention will be made apparent through the entire description of the specification.

A sensor according to one embodiment of the present invention includes a plurality of detecting units each including a pair of electrodes and a detecting area provided between the electrodes, where the detecting area is configured to causing a change in electrical resistance between the electrodes as conductive particles accumulate between the electrodes, and a sensing unit for outputting a sensing signal if at least two or more of the detecting units experience a change in electrical resistance.

In one embodiment of the present invention, the plurality of detecting units may include a first detecting unit and a second detecting unit, the first detecting unit may be constituted by a first electrode, a second electrode, and a first detecting area formed between the first and second electrodes, and the second detecting unit may be constituted by the first electrode, a third electrode, and a second detecting area formed between the first and third electrodes.

In one embodiment of the present invention, the plurality of detecting units may include a third detecting unit and a fourth detecting unit, the third detecting unit may be constituted by a fourth electrode, a fifth electrode, and a third detecting area formed between the fourth and fifth electrodes, and the fourth detecting unit may be constituted by the fourth electrode, a sixth electrode, and a fourth detecting area formed between the fourth and sixth electrodes.

In one embodiment of the present invention, the plurality of detecting units may be connected in series to each other.

In one embodiment of the present invention, the plurality of detecting units may be connected in parallel to each other.

In one embodiment of the present invention, the plurality of detecting units may each include a resistor for allowing small current to flow between the electrodes.

In one embodiment of the present invention, the sensor may include a voltage application controller unit including a power source for applying voltage to the plurality of detecting units, a signal detecting unit for detecting whether the sensing signal is output, and a storage unit for, if the sensing signal is output, storing indication that the sensing signal is output. The voltage application controller unit may stop the application of the voltage by the power source while the storage unit stores the indication that the sensing signal is output.

A sensor array relating to one embodiment of the present invention may include a plurality of sensors, where each of the sensors is the sensor described above. The sensors may be provided at different detecting positions.

Advantageous Effects

According to the present invention, there is provided a sensor capable of avoiding unexpectedly operating in response to contamination by foreign matter.

DESCRIPTION OF THE PREFERRED EMBODIMENTS

The following describes various embodiments of the present invention by referring to the appended drawings as appropriate. The constituents common to more than one drawing are denoted by the same reference signs throughout the drawings. It should be noted that the drawings are not necessarily drawn to an accurate scale for the sake of convenience of explanation.

Figure 1:
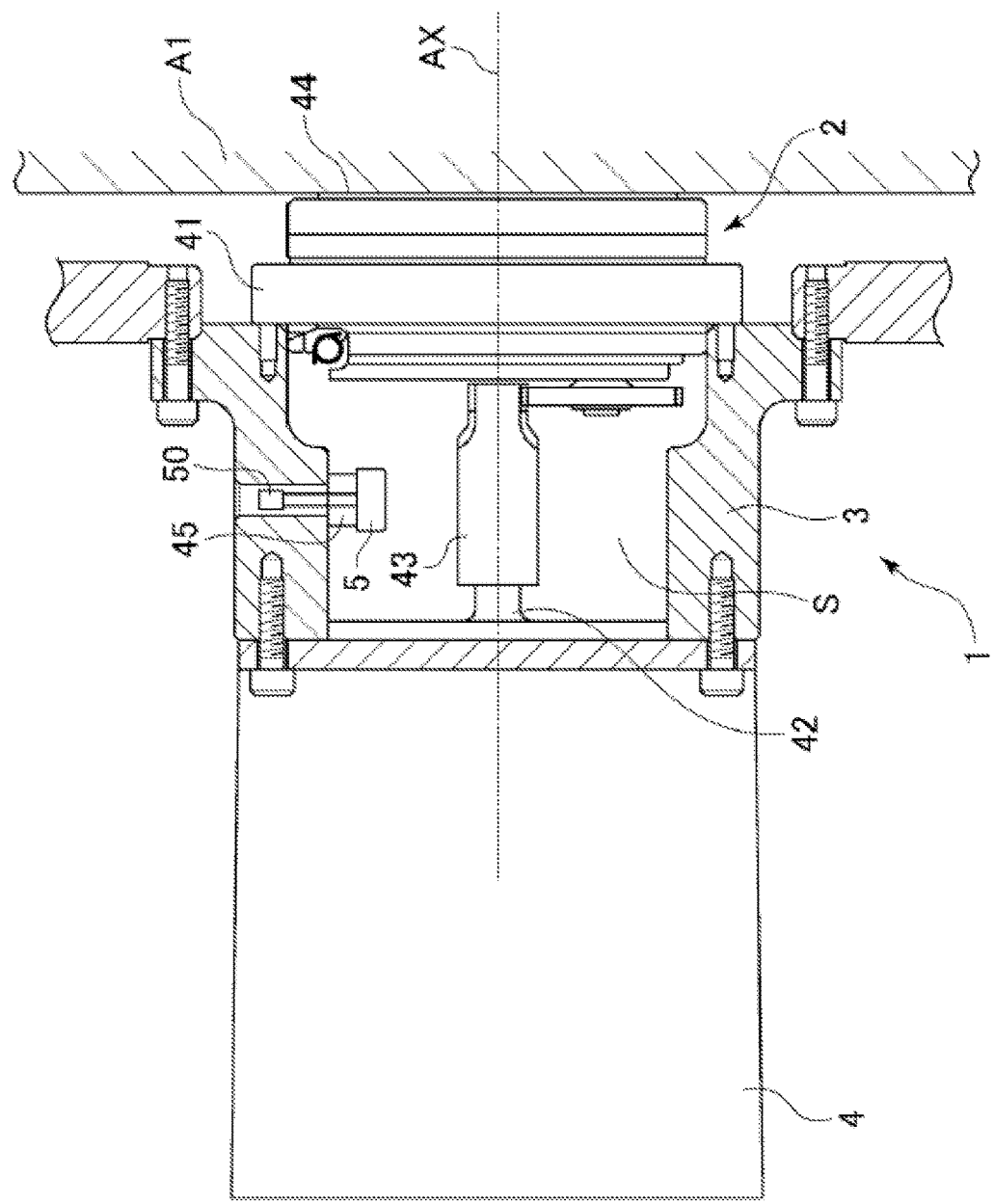
FIG. 1 is a sectional view showing one example of a mechanism including a sensor relating to one embodiment of the present invention.

FIG. 1 is a sectional view showing one example of a mechanism 1 including a sensor 5 relating to one embodiment of the present invention. The mechanism 1 is, for example, a moving part such as a robot arm. The mechanism 1 includes a speed reducer 2, a flange 3 provided on the input side, a servomotor 4, and a device A1 provided on the output side.

The speed reducer 2 includes a casing 41 mounted to the flange 3, an input shaft 43 connected to an output shaft 42 of the servomotor 4, and an output shaft 24 connected to the output-side device A1. The input shaft 43 and the output shaft 44 are supported such that they are rotatable about an axis AX relative to the casing 41. The output from the servomotor 4 is input to the speed reducer 2 via the input shaft 43, reduced by the speed reducer 2, and then transmitted to the output-side device A1 via the output shaft 44. With such arrangement, the output-side device A1 and the flange 3 are capable of rotating relative to each other.

The flange 3 is a tubular member and houses at least part of the speed reducer 2. The servomotor 4 is mounted to the flange 3. An opening in one end of the flange 3 in a direction along the axis AX is closed by the speed reducer 2, and an opening in the other end is closed by the servomotor 4. With such arrangement, the flange 3 has a tightly closed hollow portion (a space S) formed therein. The space S contains therein a lubricant oil, so that the flange 3 also serves as an oil bath.

The casing 41 of the speed reducer 2 houses therein a gear mechanism, for example. The space within the casing 41 communicates with the space S within the flange 3. As the speed reducer 2 operates, the gear mechanism in the casing 41 rotates, which subsequently causes the lubricant oil to circulate between the space in the casing 41 and the space S in the flange 10. As the lubricant oil is circulated, a conductive substance such as abrasion powder generated in the speed reducer 2 is discharged into the space S in the flange 3.

In the space S, a sensor 5 is installed for sensing the amount of the conductive substance contained in the lubricant oil. The sensor 5 is fixedly attached onto the flange 3 via, for example, a support member 45. The sensor 5 includes a magnet for attracting the conductive substance contained in the lubricant oil, so that the conductive substance accumulates between electrodes. The sensor 5 senses the amount of the conductive substance in the lubricant oil based on a change in electrical resistance between the electrodes. The sensor 5 may be alternatively positioned, for example, inside the casing 41 but can be at any position in the mechanism 1 as long as it is positioned within the space containing therein the lubricant oil.

Figure 2:
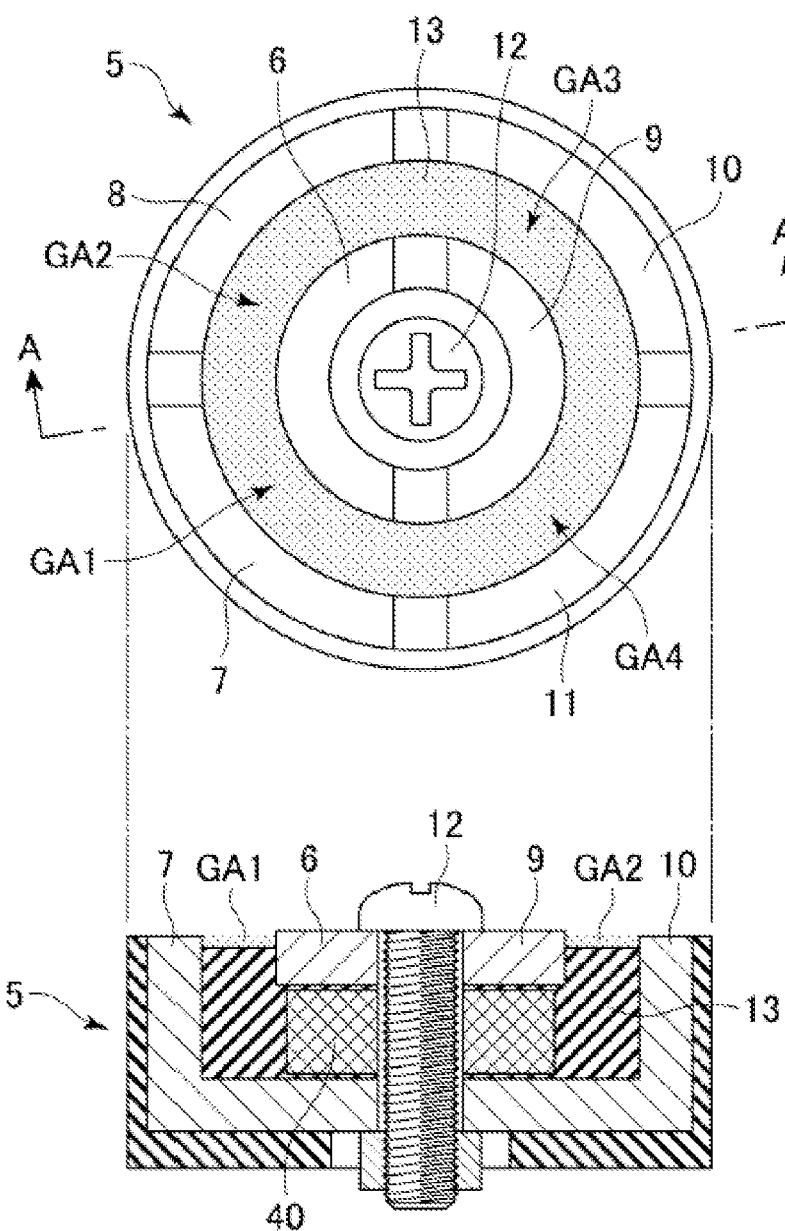
FIG. 2 shows a top view and a sectional view of a sensor according to one embodiment of the present invention.

Next, with reference to FIG. 2, a detailed description is given of the structure of the sensor 5. FIG. 2 illustrates the structure of the sensor 5 according to one embodiment of the invention. FIG. 2 shows a top view of the sensor 5 and a sectional view thereof along the A-A line in the top view.

As shown in FIG. 2, the sensor 5 has a substantially columnar outer shape and includes a plurality of detecting units and a sensing unit 50 (see FIG. 1) configured to output a signal when the detecting units experience a change in electrical resistance. The detecting units each includes a pair of electrodes and a detecting area for causing a change in electrical resistance between the paired electrodes as a conductive particle accumulates. More specifically, the sensor 5 includes a first electrode (center electrode) 6 positioned in the vicinity of the center, a second electrode (outer electrode) 7 positioned on the outer side, a third electrode (outer electrode) 8, a fourth electrode (center electrode) 9 positioned in the vicinity of the center, a fifth electrode (outer electrode) 10 positioned on the outer side, a sixth electrode (outer electrode) 11, a magnet 40, a fastening member 12, and a resin member 13. As shown in the sectional view of FIG. 2, the center electrodes 6 and 9 are positioned on the inner side relative to the outer electrodes 7, 8, 10 and 11 and spaced away from the outer electrodes 7, 8, 10 and 11. In this way, a plurality of detecting areas are formed in the resin member 13 in the upper portion thereof between (i) the center electrodes 6 and 9 and (ii) the outer electrodes 7, 8, 10 and 11.

In the illustrated embodiment, the sensor 5 includes four detecting units, and four detecting areas are formed in the upper portion of the resin member 13: a first detecting area GA1, a second detecting area GA2, a third detecting area GA3, and a fourth detecting area GA4. A first detecting unit is constituted by the first electrode 6, the second electrode 7, and the first detecting area GA1 formed between the first and second electrodes 6 and 7. A second detecting unit is constituted by the first electrode 6, the third electrode 8, and the second detecting area GA2 formed between the first and third electrodes 6 and 8. A third detecting unit is constituted by the fourth electrode 9, the fifth electrode 10, and the third detecting area GA3 formed between the fourth and fifth electrodes 9 and 10. A fourth detecting unit is constituted by the fourth electrode 9, the sixth electrode 11, and the fourth detecting area GA4 formed between the fourth and sixth electrodes 9 and 11. It should be noted that the magnet 40 may not be used, in which case the center electrode 6 may be configured to serve not only as the electrode and but also as the magnet 40.

The electrodes are magnetic members formed of an electrically conductive magnetic material such as iron, ferrite, or silicon steel. Between the electrodes, there is disposed the resin material 13, which is a non-magnetic material (an insulator). The electrodes and magnet 40 are buried at least partly in the central region of the resin member. The shape of the electrodes and magnet 40 is not limited to the illustrated example, and the electrodes and magnet 40 can be shaped variously.

The center electrodes 6 and 9 and the outer electrodes 7, 8, 10 and 11 are each connected to an output line (not shown). The magnet 40 may or may not be attached to, for example, the bottom of the center electrodes 6 and 9. When the magnet 40 is attached, the magnet 40 is formed of a magnet or electromagnet, and the magnet may be covered with a nonmagnetic material such as copper and a signal line (not shown) may be connected to the covering layer. The magnet 40 forms lines of magnetic flux around the detecting areas GA1, GA2, GA3 and GA4. Thus, the conductive substance contained in the lubricant oil is gathered to the vicinity of the detecting areas GA1, GA2, GA3 and GA4.

The sensor 5 is connected to the sensing unit 50 including a sensor drive circuit (not shown) that monitors the resistance of the sensor 5 to predict a failure of the mechanical parts based on a change in the resistance caused by the accumulation of the conductive substance between the electrodes. When a certain amount of conductive substance accumulates in the detecting area, the electrical resistance between (i) the electrodes 6 and 9 to which a voltage is applied and (ii) at least one of the electrode 7, 8, 10 or 11 (in other words, one of the detecting units) drops (in other words, a short circuit occurs), and the output level of the output line changes. The sensor drive circuit in the sensing unit 50 detects the change in the electrical resistance to predict a failure of the mechanical parts. The drop in electrical resistance may be indicated by an ON/OFF signal determined by whether electrical connection is established or not, so that the drop in electrical resistance may be sensed between the two states of electrical disconnection and electrical connection (hereinafter referred to as "digital sensing").

The sensor drive circuit is connected to a higher-level control device such as a manipulator in a wired or wireless manner. A circuit board 43 shown in FIG. 1 may transmit the output on the output line (the output from the sensor 5) to the higher-level control device either constantly or intermittently (at predetermined time intervals) for saving electricity.

When sensing a change in the output level of the output line received from the circuit board 43, the higher-level control device may be configured to issue a warning via a predetermined notification unit (a display or voice output device) for demanding maintenance of, for example, the speed reducer 2.

Figure 3:
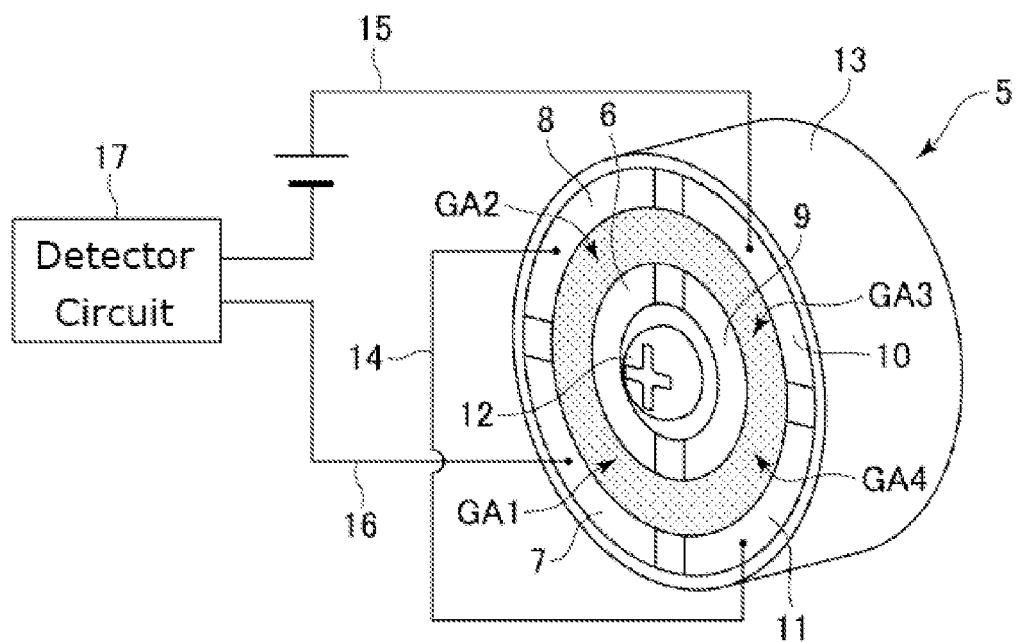
FIG. 3 schematically shows how connections are done in a sensor according to one embodiment of the present invention.

Next, with reference to FIG. 3, a description is given of how connections are done in the sensor 5 according to one embodiment of the present invention. As illustrated, the fifth electrode (outer electrode) 10 positioned on the outer side is connected to a detector circuit 17 via a connection line 15, and the second electrode (outer electrode) 7 positioned on the outer side is connected to the detector circuit 17 via a connection line 16. In addition, as illustrated, the third electrode (outer electrode) 8 and the sixth electrode (outer electrode) 11 are connected to each other via a connection line 14. In this way, the sensor 5 can be configured such that a logical AND can be obtained between four circuits in the order of the fifth electrode (outer electrode) 10, fourth electrode (center electrode) 9 in the vicinity of the center, sixth electrode (outer electrode) 11, third electrode (outer electrode) 8, the first electrode (center electrode) 6 in the vicinity of the center, and second electrode (outer electrode) 7. Such a configuration can be achieved with a reduced number of lead wires, or requires only two lead wires. In the case where the first and fourth electrodes (center electrodes) 6 and 9 in the vicinity of the center are integrally formed, five lead wires are required to take care of the respective outer electrodes 7, 8, 10 and 11. With the above-described configuration, however, the number of lead wires can be significantly reduced.

According to the configuration shown in FIG. 3, voltage is applied between the second and fifth electrodes 7 and 10, and a short circuit occurs between the third and sixth electrodes 8 and 11. Accordingly, the first detecting area GA1 between the first electrode (center electrode) 6 in the vicinity of the center and the second electrode (outer electrode) 7, the second detecting area GA2 between the first electrode (center electrode) 6 in the vicinity of the center and the third electrode (outer electrode) 8, the third detecting area GA3 between the fourth electrode (center electrode) 9 in the vicinity of the center and the fifth electrode (outer electrode) 10, and the fourth detecting area GA4 between the fourth electrode (center electrode) 9 in the vicinity of the center and the sixth electrode (outer electrode) 11 are connected in series to constitute a circuit. Since the plurality of detecting units are connected to each other in series as described above, the present embodiment can prevent a foreign substance from causing the sensor 5 to unexpectedly operating. Specifically, cutting chips or the like may possibly remain in the lubricant oil, but the detector circuit can avoid transmitting an erroneous signal unless the cutting chips adhere to all of the detecting areas.

Figure 4:
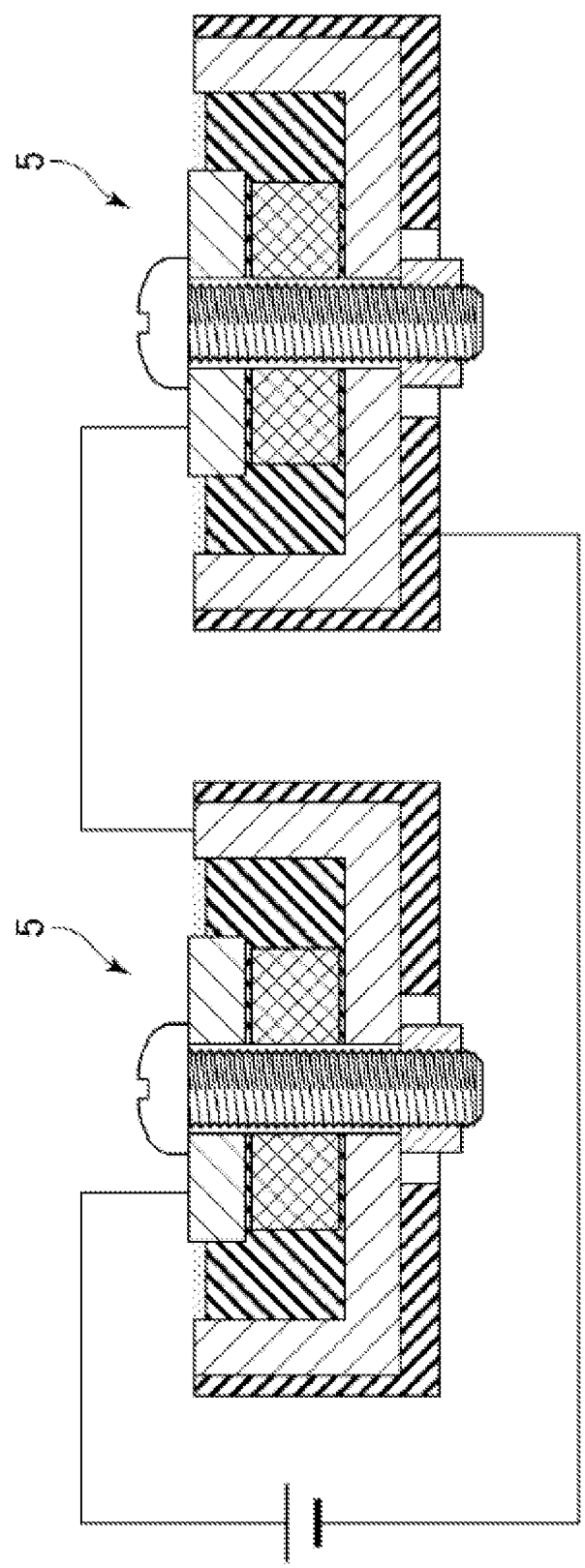
FIG. 4 schematically shows how sensors are connected in one embodiment of the present invention.

The following describes an array of sensors (a group of sensors) constituted by a plurality of sensors with reference to FIG. 4. A plurality of sensors 5 are provided at different detecting positions. In the illustrated embodiment, an array of sensors (a group of sensors) includes two sensors 5 and is configured such that the sensors 5 can respectively detect the amount of conductive substance at two detecting positions. The numbers of detecting positions and sensors 5 are not limited to such and may be changed as the case may be. For example, in a case where the lubricant oil is contained in a space S (see FIG. 1) having a sufficiently large volume, a single sensor 5 may encounter difficulties in successful sensing. If a plurality of detecting positions are defined and one or more sensors are provided at each detecting position, the sensing can be accurately performed.

According to one of the examples of the above configuration, the two sensors 5 are connected in series to constitute a circuit as illustrated. Since the two sensors 5 are arranged in series, the conductive substance adhering to the sensor 5 in only one of the detecting areas is not enough to cause current to flow through the circuit, and current flows through the circuit only if the conductive substance adheres also to the sensor 5 in the other detecting area. In this manner, the array of sensors relating to one embodiment of the present invention can reliably avoid making an output relating to failure prediction when one of the sensors 5 erroneously predict failure.

Figure 5:
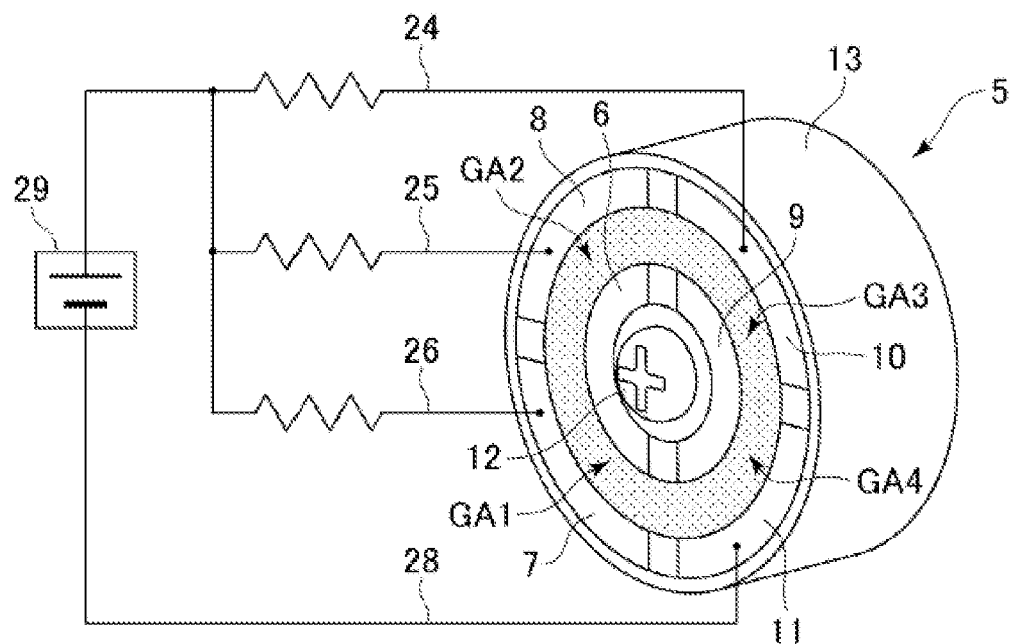
FIG. 5 schematically shows how connections are done in a sensor according to one embodiment of the present invention.

The following describes how connections are done in the sensor 5 relating to one embodiment of the present invention with reference to FIG. 5. As shown, while a plurality of detecting areas are formed in the same manner as described with reference to FIG. 3, the second, third and fifth electrodes 7, 8 and 10 are connected in parallel using connection lines 24, 25 and 26, and these electrodes are connected to the sixth electrode 11 in series using a connection line 28. The electrodes 7, 8, 10 and 11 are connected to a detector circuit 29 including a voltage source.

As shown in FIG. 5, one of the four outer electrodes (i.e., the second, third, fifth and sixth electrodes 7, 8, 10 and 11) is multiplexed (Gnd), and the remaining three outer electrodes can be used as a signal. Electrical connection is established between the first and fourth electrodes 6 and 9 as conductive particles accumulate. The centrally arranged circular electrode connects together the two sections of the sensor 5 in series, one of which includes the three elements connected in parallel. With such configuration, the voltage can be approximately halved and improved robustness can be resultantly achieved against disconnection.

Figure 6:
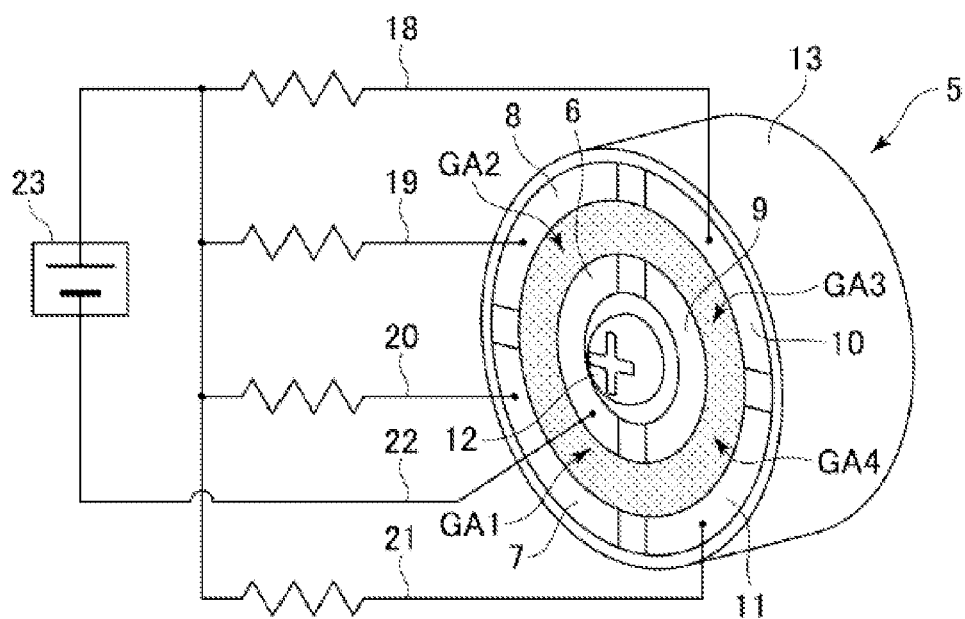
FIG. 6 schematically shows how connections are done in a sensor according to one embodiment of the present invention.

Next, with reference to FIG. 6, a description is given of how connections are done in a sensor 5 according to another embodiment of the present invention. The sensor 5 shown in FIG. 6 has the same configuration as the sensor shown in FIG. 3, but is connected to a detector circuit in a different manner than in FIG. 3. In the sensor 5 shown in FIG. 6, the second, third, fifth and sixth electrodes 7, 8, 10 and 11 are connected in parallel using connection lines 18, 19, 20 and 21, and these electrodes are connected to a detector circuit 23 including a voltage source.

Since the four outer electrodes (i.e., the second, third, fifth and sixth electrodes 7, 8, 10 and 11) are connected together in parallel as shown in FIG. 6, the voltage can be approximately quartered when compared with the case where the four outer electrodes are connected in series with each other. At the same time, improved robustness can be achieved against disconnection since the Gnd line is multiplexed FIG. 7 shows a top view of a sensor 5 according to another embodiment of the invention and a sectional view taken along the line A-A.

Figure 7:
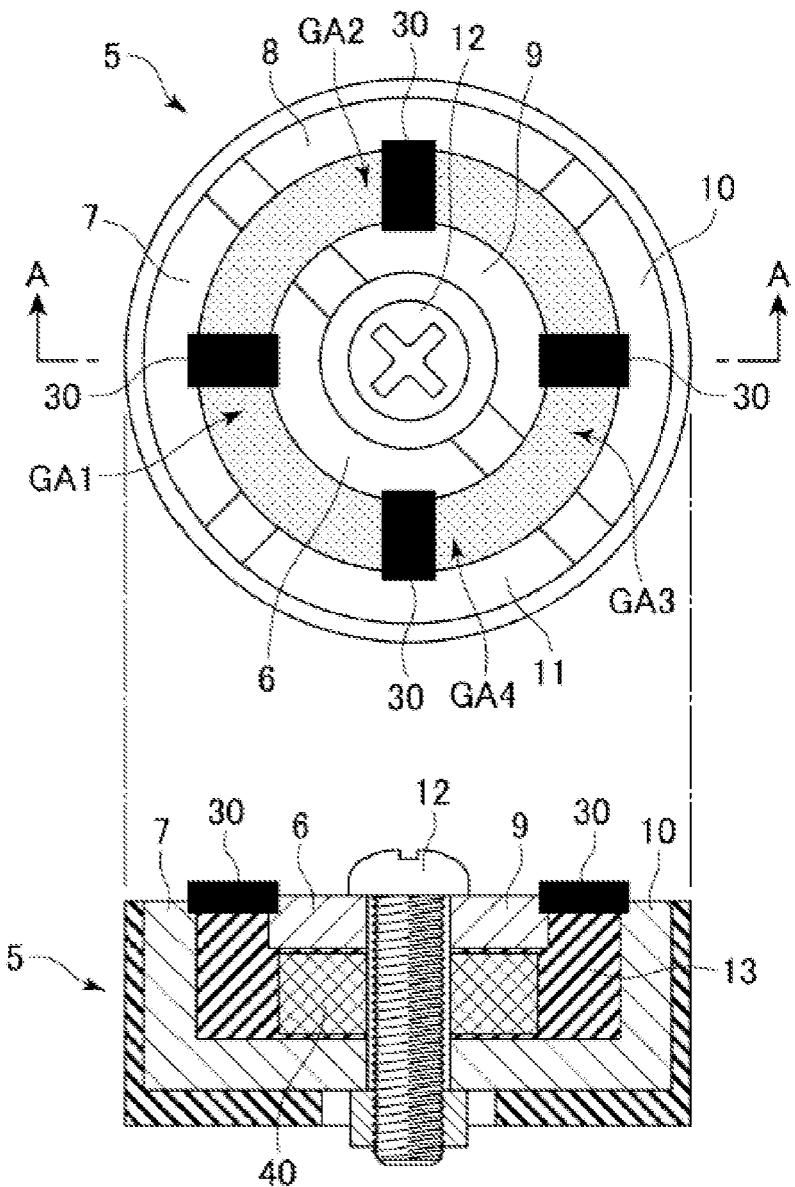
FIG. 7 shows a top view and a sectional view of a sensor according to one embodiment of the present invention.

As shown in FIG. 7, the sensor 5 according to another embodiment of the present invention includes a first electrode (center electrode) 6 in the vicinity of the center, a second electrode (outer electrode) 7 positioned on the outer side, a third electrode (outer electrode) 8, a fourth electrode (center electrode) 9 in the vicinity of the center, a fifth electrode (outer electrode) 10 positioned on the outer side, a sixth electrode (outer electrode) 11, a magnet 40, a fastening member 12 and a resin member 13.

In the illustrated embodiment, resistors 30 are provided on the resin member 13 such that they are respectively positioned between the first electrode (center electrode) 6 and the second electrode (outer electrode) 7, between the first electrode (center electrode) 6 and the third electrode (outer electrode) 8, between the fourth electrode (center electrode) 9 and the fifth electrode (outer electrode) 10, and between the fourth electrode (center electrode) 9 and the sixth electrode (outer electrode) 11. In other words, a plurality of detecting units included in the sensor 5 each further include the resistor 30 for allowing a small current to flow between the electrodes constituting the detecting unit. FIG. 7 shows only an example of how the resistors 40 can be arranged. The shape, structure, location and arrangement of the resistors 30 are not limited in any particular manner and can be changed as the case may be.

In the present embodiment, detecting areas GA1, GA2, GA3 and GA4 of the sensor 5 each has the resistor 30 exhibiting high resistance connected thereto. In this manner, a small current can flow between the electrodes via the resistor 30 if only a small amount of conductive substance accumulates. With such configurations, the small current stops flowing if the copper lines (the connection lines and the like) are broken. Accordingly, disconnection of the circuit can be detected. The resistance R of the resistor 30 is sufficiently higher than the resistance Ω exhibited by the gap portion when a failure is detected. If the speed reducer fails, the conductive substance gathers resultantly, the resistance of the detecting areas then drops, and a large current is allowed to flow. Considering this, a threshold value may be set for the current, so that the failure can be predicted. With the above-described configurations, both of the circuit disconnection detection and the failure prediction can be reliably achieved.

In the sensor relating to one embodiment of the present invention, once the conductive substance adheres to the sensor to such an extent that the current exceeds the threshold, the sensor may be resultantly turned on. This causes the current to flow constantly and may possibly waste the energy. In addition, this may affect the lifetime of a photo coupler (PC) and cause problems such as breakage of the circuit since the lifetime of the photo coupler (PC) correlatively depends on the duration of the current flow.

Figure 8:
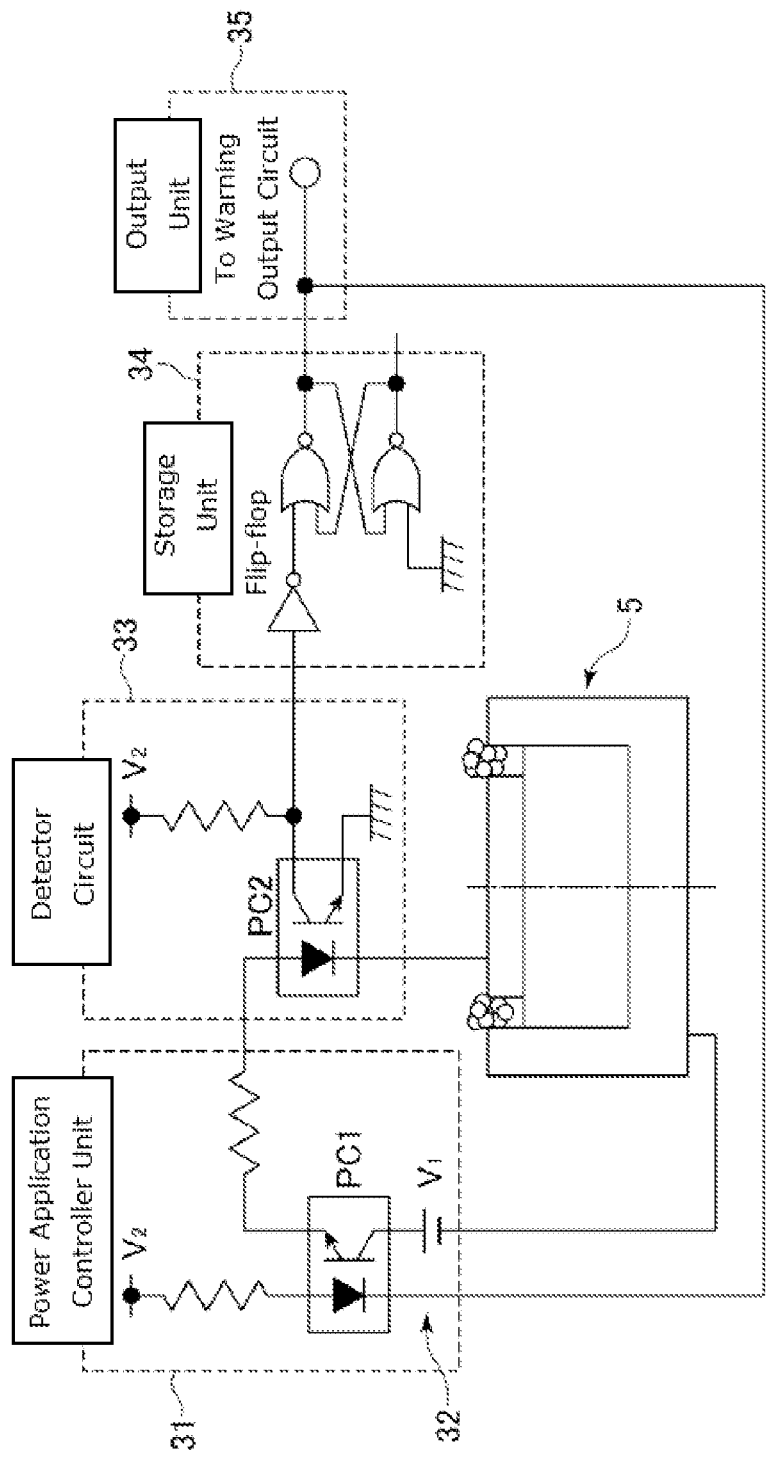
FIG. 8 schematically shows a signal processing circuit including a sensor relating to one embodiment of the present invention.

FIG. 8 is used to illustrate the configuration of a signal processing circuit provided to overcome such problems. As shown in FIG. 8, the sensor 5 is connected via a connection line to a power application controller unit 31 including a power source 32 and then to a voltage detector unit 33, a storage unit 34 and an output unit 35. The storage unit 34 is connected to the power application controller unit 31 via a connection line.

The power application controller unit 31 shown includes the power source 32 configured to apply voltage between the electrodes of the sensor 5, and is configured to stop the application of the voltage by the power source 32. The voltage detector unit 33 is configured to detect whether the power source 32 applies voltage and outputs a sensing signal in response to detecting the application. The storage unit 34 stores the output sensing signal if the voltage detector unit 33 outputs the sensing signal. The storage unit 34 shown indicates an RS flip-flop storing a state, but may be alternatively an integrated device including, for example, a memory of a microcomputer or configured in any other manners. Once the storage unit 34 stores thereon the sensing signal, the output unit 35 outputs indication indicating that the sensing signal has been output and generates a trigger for a warning indicating predicted failure.

If the amount of the conductive substance adhering to the sensor 5 relating to one embodiment of the present invention exceeds a threshold, current flows between the sensor 5 and the power source 32 (the ON state). Once detecting the ON state, the detector unit 33 outputs a sensing signal to the storage unit 34, and the storage unit 34 stores the sensing signal. Once storing the sensing signal, the storage unit 34 enters the Hi state. As a result, the power application controller unit 31 also enters the Hi state, which stops the application of the voltage and turns off a PC1. This turns off the power fed to the sensor 5. Accordingly, the output from the detector unit 33 to the storage unit 34 changes, but the circuit of the storage unit 34 is configured such that the output from the storage unit 34 remains unchanged. Therefore, the output unit keeps generating a trigger for a warning indicating predicted failure.

In the above-described manner, the present embodiment can prevent current from continuously flowing through the circuit and thus achieve an extended lifetime for the photo-couplers (PC), thereby avoiding breakage of the circuit.

Figure 9:
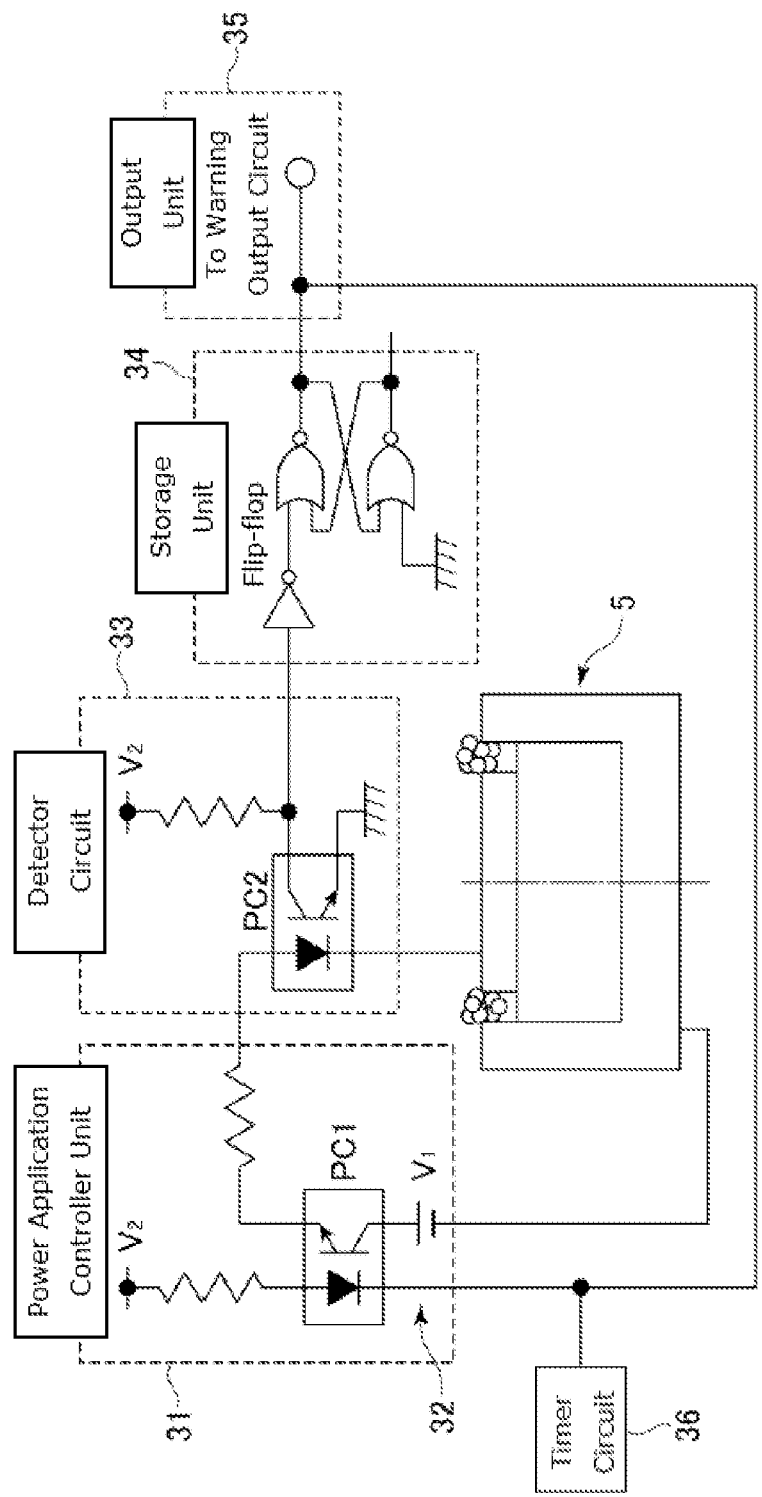
FIG. 9 schematically shows a signal processing circuit including a sensor relating to one embodiment of the present invention.

FIG. 9 is used to illustrate a different configuration of the signal processing circuit. As shown in FIG. 9, the sensor 5 is connected via a connection line to a power application controller unit 31 including a power source 32 and then to a voltage detector unit 33, a storage unit 34 and an output unit 35. The storage unit 34 is connected to the power application controller unit 31 via a connection line. Unlike the case shown in FIG. 8, a timer circuit 36 is connected between the storage unit 34 and the power application controller unit 31.

The power application controller unit 31 shown includes the power source 32 configured to apply voltage between the electrodes of the sensor 5, and is configured to stop the application of the voltage by the power source 32. The voltage detector unit 33 is configured to detect whether the power source 32 applies voltage and outputs a sensing signal in response to detecting the application. The storage unit 34 stores the output sensing signal if the voltage detector unit 33 outputs the sensing signal. The storage unit 34 shown indicates an RS flip-flop storing a state, but may be alternatively an integrated device including, for example, a memory of a microcomputer or configured in any other manners. Once the storage unit 34 stores thereon the sensing signal, the output unit 35 outputs indication indicating that the sensing signal has been output and generates a trigger for a warning indicating predicted failure.

If the amount of the conductive substance adhering to the sensor 5 relating to one embodiment of the present invention exceeds a threshold, current flows between the sensor 5 and the power source 32 (the ON state). Once detecting the ON state, the detector unit 33 outputs a sensing signal to the storage unit 34, and the storage unit 34 stores the sensing signal. Since the conductive substance typically tends to increase gradually, it is not necessarily required to keep applying voltage constantly to the sensor 5 to keep monitoring the sensor 5. Intermittent monitoring is effectively used to predict a failure.

The signal processing circuit shown in FIG. 9 additionally includes the timer circuit 36, so that the voltage is applied at predetermined time intervals or at every predetermined time. In this manner, the present embodiment can prevent current from continuously flowing through the circuit, thereby reducing energy consumption.

The embodiments of the present invention are not limited to the above examples but can be modified variously within the scope of the technical idea of the present invention. For example, the embodiments of the present invention include combinations of the above examples described herein and obvious embodiments.

LIST OF REFERENCE NUMBERS

1 mechanism
2 speed reducer
3 flange portion
4 servomotor
5 sensor
6 first electrode (center electrode)
7 second electrode (outer electrode)
8 third electrode (outer electrode)
9 fourth electrode (center electrode)
10 fifth electrode (outer electrode)
11 sixth electrode (outer electrode)
12 screw member
13 resin
14 connection line
15 connection line
16 connection line
17 detector circuit
18 connection line
19 connection line
20 connection line
21 connection line
22 connection line
23 detector circuit
24 connection line
25 connection line
26 connection line
28 connection line
29 detector circuit
30 resistor
31 power application controller unit
32 power source
33 voltage detector unit
34 storage unit
35 output unit
36 timer circuit
40 magnet
43 circuit board

What is claimed is:

1. A sensor comprising:
 a plurality of detecting units each including a pair of electrodes and a detecting area provided between the electrodes, the detecting area being configured to cause a change in electrical resistance between the electrodes as conductive particles accumulate between the electrodes, the plurality of detecting units being arranged in lubricant containing the conductive particles;
 a sensing unit for outputting a sensing signal if at least two or more of the detecting units experience a change in electrical resistances;
 a voltage application controller unit including a power source for applying voltage to the plurality of detecting units;
 a signal detecting unit for detecting whether the sensing signal is output; and
 a storage unit for, if the sensing signal is output while the plurality of detecting units are in the lubricant, storing indication that the sensing signal is output, and
 wherein the voltage application controller unit stops the application of the voltage by the power source while the plurality of detecting units remain in the lubricant and the storage unit stores the indication that the sensing signal is output.

2. The sensor of claim 1, wherein the plurality of detecting units include a first detecting unit and a second detecting unit,
 wherein the first detecting unit is constituted by a first electrode, a second electrode, and a first detecting area formed between the first and second electrodes, and
 wherein the second detecting unit is constituted by the first electrode, a third electrode, and a second detecting area formed between the first and third electrodes.

3. The sensor of claim 2, wherein the plurality of detecting units include a third detecting unit and a fourth detecting unit,
 wherein the third detecting unit is constituted by a fourth electrode, a fifth electrode, and a third detecting area formed between the fourth and fifth electrodes, and
 wherein the fourth detecting unit is constituted by the fourth electrode, a sixth electrode, and a fourth detecting area formed between the fourth and sixth electrodes.

4. The sensor of claim 1, wherein the plurality of detecting units are connected to each other in series.

5. The sensor of claim 1, wherein the plurality of detecting units are connected to each other in parallel.

6. The sensor of claim 1, wherein the plurality of detecting units each include a resistor for allowing small current to flow between the electrodes.

7. A sensor array comprising a plurality of sensors, each sensor being the sensor of claim 1, wherein the plurality of sensors are provided at different detecting positions.

* * * * *